(12) United States Patent
Xu et al.

(10) Patent No.: US 10,648,975 B2
(45) Date of Patent: May 12, 2020

(54) SINGLE CHANNEL CHEMILUMINESCENT MICRO-FLUIDIC CHIP AND DETECTION METHOD THEREOF

(71) Applicant: NANJING LANSION BIOTECHNOLOGY CO., LTD., Nanjing, Jiangsu (CN)

(72) Inventors: Xingshang Xu, Jiangsu (CN); Jeffery Chen, Jiangsu (CN); Long Wang, Jiangsu (CN); Weiyan Sun, Jiangsu (CN); Qilu Wan, Jiangsu (CN); Shen Yang, Jiangsu (CN)

(73) Assignee: LANSION BIOTECHNOLOGY CO., LTD., Nanjing (CN)

( * ) Notice: Subject to any disclaimer, the term of this patent is extended or adjusted under 35 U.S.C. 154(b) by 0 days.

(21) Appl. No.: 16/079,440

(22) PCT Filed: Dec. 6, 2017

(86) PCT No.: PCT/CN2017/114692
§ 371 (c)(1),
(2) Date: Aug. 23, 2018

(87) PCT Pub. No.: WO2019/006978
PCT Pub. Date: Jan. 10, 2019

(65) Prior Publication Data
US 2019/0137487 A1    May 9, 2019

(30) Foreign Application Priority Data

Jul. 3, 2017 (CN) .......................... 2017 1 0531301

(51) Int. Cl.
| | | |
|---|---|---|
| G01N 33/558 | (2006.01) | |
| B01L 3/00 | (2006.01) | |
| F16K 99/00 | (2006.01) | |
| G01N 33/543 | (2006.01) | |

(52) U.S. Cl.
CPC .......... *G01N 33/558* (2013.01); *B01L 3/5027* (2013.01); *F16K 99/0042* (2013.01); *G01N 33/54393* (2013.01)

(58) Field of Classification Search
CPC ............ G01N 33/558; G01N 33/54393; B01L 3/5027; F16K 99/0042
See application file for complete search history.

(56) References Cited

U.S. PATENT DOCUMENTS

| | | | | |
|---|---|---|---|---|
| 6,637,463 B1 * | 10/2003 | Lei | .......................... | B01F 5/0403 137/803 |
| 9,121,847 B2 * | 9/2015 | Kamm | ..................... | C12Q 1/02 |
| 10,427,156 B2 * | 10/2019 | Peumans | .................. | G01N 1/14 |
| 2003/0134416 A1 | 7/2003 | Yamanishi | | |
| 2003/0198576 A1 | 10/2003 | Coyne et al. | | |
| 2005/0118730 A1 * | 6/2005 | Kogi | ..................... | B01J 19/0046 436/518 |
| 2007/0248958 A1 | 10/2007 | Jovanovich et al. | | |
| 2009/0060787 A1 * | 3/2009 | Kim | .................. | B01L 3/502746 422/68.1 |
| 2010/0068723 A1 | 3/2010 | Jovanovich | | |
| 2012/0088249 A1 | 4/2012 | Jovanovich et al. | | |
| 2012/0149872 A1 * | 6/2012 | Belgrader | ............ | B01D 15/161 530/344 |
| 2013/0029338 A1 | 1/2013 | Jovanovich et al. | | |
| 2014/0038209 A1 | 2/2014 | Shih et al. | | |
| 2014/0087359 A1 * | 3/2014 | Njoroge | ................. | C12N 1/066 435/2 |
| 2015/0118728 A1 * | 4/2015 | Rahman | ............ | B01L 3/502753 435/173.9 |
| 2019/0137488 A1 | 5/2019 | Xu et al. | | |

FOREIGN PATENT DOCUMENTS

| | | |
|---|---|---|
| CA | 2462914 A1 | 4/2003 |
| CN | 101073002 A | 11/2007 |
| CN | 101692047 A | 4/2010 |
| CN | 102759466 A | 10/2012 |
| CN | 103566984 A | 2/2014 |
| CN | 105203746 A | 12/2015 |
| CN | 105214744 A | 1/2016 |
| CN | 205308354 U | 6/2016 |
| CN | 105879936 A | 8/2016 |
| CN | 205517819 U | 8/2016 |
| CN | 106215985 A | 12/2016 |
| CN | 106902904 A | 6/2017 |
| CN | 106902905 A | 6/2017 |
| CN | 107219360 | 9/2017 |
| CN | 107225006 A | 10/2017 |
| DK | 1439897 T3 | 1/2011 |
| EP | 2156879 A2 | 2/2010 |
| EP | 2261650 A2 | 12/2010 |
| EP | 3470143 A1 | 4/2019 |

(Continued)

*Primary Examiner* — Ann Y Lam
(74) *Attorney, Agent, or Firm* — Anna Tsang

(57) ABSTRACT

Provided is a single-channel chemiluminescent micro-fluidic chip, including a chip body with a quantification-reaction cavity and a waste liquid cavity. The quantification-reaction cavity is composed of a quantification-reaction pool on a lower portion and a reaction pool cover plate, the quantification-reaction pool is equally divided into three cavities by two partition plates, a labeled antibody is placed in the middle cavity, coated antibodies are placed in the others, a surface, facing the quantification-reaction pool, of the reaction pool cover plate is equally divided into two parts. In result, the coated antibodies and the labeled antibodies are physically separated to effectively avoid nonspecific binding. Due to a special structure of the reaction tank, wavy fluid flow is generated to fully mix the coated antibodies and the labeled antibodies, which improves testing efficiency and sensitivity.

8 Claims, 10 Drawing Sheets

(56) References Cited

FOREIGN PATENT DOCUMENTS

| | | |
|---|---|---|
| JP | 2008513022 A | 5/2008 |
| JP | 2012189615 A | 10/2012 |
| JP | 201432171 A | 2/2014 |
| JP | 5759656 B2 | 8/2015 |
| JP | WO2014069551 A1 | 9/2016 |
| JP | 6090330 B2 | 3/2017 |
| KR | 20070063542 A | 6/2007 |
| KR | 20140017418 A | 2/2014 |
| TW | 201407161 A | 2/2014 |
| WO | 03031938 A2 | 4/2003 |
| WO | 03072254 A1 | 9/2003 |
| WO | 03098218 A1 | 11/2003 |
| WO | WO 03098218 * 11/2003 | ........... G01N 33/558 |
| WO | 2006032044 A2 | 5/2006 |
| WO | 2013158044 A1 | 10/2013 |
| WO | 2014078775 A1 | 5/2014 |

* cited by examiner

SINGLE CHANNEL CHEMILUMINESCENT MICRO-FLUIDIC CHIP AND DETECTION METHOD THEREOF

BACKGROUND OF THE INVENTION

Technical Field

The present invention relates to a single-channel chemiluminescent micro-fluidic chip and a detection method thereof, and belongs to the technical field of lateral flow immunoassay.

Description of Related Art

As a stable and practical technique, lateral flow immunoassay is suitable for point-of-care testing (POCT) of various types or field service.

In an immunochromatographic reaction system, the coefficient of variation (CV) is large due to system factors, and consequentially, precise quantification cannot be achieved. Immunodiagnosis methods based on the micro-fluidic technology can effectively solve these problems.

Micro-fluidic includes passive micro-fluidic and active micro-fluidic, wherein passive micro-fluidic still relies on capillary force to achieve forward lateral chromatography of fluid. However, due to different viscosities of different samples and particularly whole blood samples, uniform fluid velocities are unavailable.

Active micro-fluidic can effectively solve the aforesaid problem and can provide forward thrust to make fluid evenly flow forwards, thereby avoiding test value discrepancies caused by different flow velocities.

Power for active micro-fluidic includes centrifugal force drive, electric wetting drive and pressure drive (electrolytic pumps, compressed air pumps, chemical decomposition pumps and direct pressure differential drive).

However, in order to control the fluid velocity at will, besides the thrust, valve control and backflow prevention measures for preventing backflow of fluid after pressure relief are also indispensable.

Please refer to the following patents in the prior art for chip manufacturing and application:

(1) CN203899622U Micro-fluidic Chip
(2) CN106353491A Micro-fluidic Beside Rapid Diagnosis Kit
(3) CN205941345U Micro-fluidic Chip for Biological Detection Wherein, in Patent (2) and Patent (3), a fluid sample added into a chip is not quantified; however, in order to realize quantitative detection, the sample added into the chip and a reagent pre-stored in the chip must be quantified Monitoring of the accurate position of fluid flowing in the chip is involved in none of Patent (1), Patent (2) and Patent (3), which means that in these three aforesaid patents, the filling behavior of fluid in a passage or cavity in the chip is not monitored before the final detection result of the chip comes out.

In addition, in the prior art, a labeled antibody and a coated antibody are placed in different cavities to prevent nonspecific binding of the labeled antibody and the coated antibody, which is not beneficial to structural simplification of the chip; and meanwhile, the coated antibody and the labeled antibody cannot be sufficiently mixed in the reaction process, thus, affecting testing efficiency.

BRIEF SUMMARY OF THE INVENTION

In order to overcome the defects of the prior art, the present invention provides a single-channel chemiluminescent micro-fluidic chip. According to the single-channel chemiluminescent micro-fluidic chip, coated antibodies and labeled antibodies are ingeniously placed in one reaction tank to simplify the reagent operation process; and meanwhile, the coated antibodies and the labeled antibodies are physically separated to effectively avoid nonspecific binding. Furthermore, the reaction tank is designed into a special structure, so that when fluid flows through the reaction tank, wavy fluid flow is generated to fully mix the coated antibodies and the labeled antibodies, and thus, testing efficiency and sensitivity are effectively improved.

To realize the above technical objective, the following technical scheme is adopted by the present invention.

A single-channel chemiluminescent micro-fluidic chip, including a chip body, wherein the chip body includes an optical path scanning window, a whole blood filter cavity, a quantification-reaction cavity and a waste liquid cavity, a fluid outlet of the whole blood filter cavity is sequentially communicated with the quantification-reaction cavity and the waste liquid cavity through a micro-fluidic passage, the optical path scanning window is disposed over the quantification-reaction cavity, a fluid inlet of the quantification-reaction cavity is communicated with external fluid paths through a cleaning solution delivery branch and a chromogenic reagent delivery branch respectively, and the whole blood filter cavity is communicated with an external air path; characterized in that the quantification-reaction cavity is composed of a quantification-reaction pool on a lower portion and a reaction pool cover plate for sealing an opening of the quantification-reaction pool, the quantification-reaction pool is equally divided into three cavities by two partition plates a disposed perpendicular to a fluid flow direction, a labeled antibody is placed in the middle cavity, coated antibodies are placed in the partitioned cavities on two sides, a surface, facing the quantification-reaction pool, of the reaction pool cover plate is equally divided into two cover plate parts by a partition plate b disposed perpendicular to the fluid flow direction, and the coated antibodies are embedded in the cover plate parts.

As a further improvement of the present invention, the fluid outlet of the whole blood filter cavity is communicated with the fluid inlet of the quantification-reaction cavity through a first anti-backflow device, and a fluid outlet of the cleaning solution delivery branch and a fluid outlet of the chromogenic reagent delivery branch are converged and then communicated with the fluid inlet of the quantification-reaction pool through a second anti-backflow device; the first anti-backflow device and the second anti-backflow device are of the same structure and each includes an anti-backflow structure located above the micro-fluidic passage and provided with an anti-backflow passage for increasing a liquid level of the micro-fluidic passage at an anti-backflow structure mounting position; and when the micro-fluidic passage is communicated with the external air path, fluid in the micro-fluidic passage through both sides of each said anti-backflow device is driven by air from the external air path to circulate by overcoming a pressure generated by the liquid level, increased by the corresponding anti-backflow passage at the corresponding anti-backflow structure mounting position, of the micro-fluidic passage.

As a further improvement of the present invention, a valve device is disposed on the micro-fluidic passage between the quantification-reaction cavity and the waste liquid cavity and includes a detection mechanism used to sense whether or not fluid flows through a valve device mounting position; the valve device in a normally-open state in the chip body automatically closes to be in an interruption state when a numerical value fed back by the detection mechanism indicates that fluid flows through the valve device mounting position, and the valve device in the interruption state is regularly opened to be in a circulation state; and when the valve device is in the circulation state, fluid is pushed by air flow from the external air path to circulate in the valve device.

As a further improvement of the present invention, first absorbent paper is disposed in the waste liquid cavity, and the waste liquid cavity is provided with two waste cavity parts communicated with each other, namely a waste liquid cavity part a and waste liquid cavity part b, wherein an air flow channel is formed between an inner wall of the waste liquid cavity part a and the first absorbent paper, and the waste liquid cavity part b is provided with an air outlet.

As a further improvement of the present invention, the waste liquid cavity includes a waste liquid pool, a middle cover plate for sealing an opening of the waste liquid pool, and an upper cover plate for covering the middle cover plate; a plurality of waste liquid guiding components are disposed on a wall, corresponding to the waste liquid cavity part a, of the waste liquid pool, and absorbent paper fixing columns are disposed at a bottom of the waste liquid pool and are adjacent to the waste liquid guiding components; the waste liquid guiding components are each in an arc tooth shape and sequentially disposed on the corresponding wall of the waste liquid pool in respective are directions, the first absorbent paper is disposed in the waste liquid pool through absorbent paper fixing columns, and a side edge of the first absorbent paper makes contact with tips of the waste liquid guiding components; the middle cover plate is provided with a middle through hole, communicated with the opening of the waste liquid pool, at a position corresponding to the waste liquid cavity part a and a middle vent hole, communicated with the opening of the waste liquid pool, at a position corresponding to the waste liquid cavity part b; an absorbent paper groove is formed in a position of the middle vent hole, and second absorbent paper is disposed in the absorbent paper groove; and the upper cover plate is provided with a vent hole sealing cover, used to cover the middle vent hole, at a position corresponding to the middle vent hole and an upper vent hole, communicated with the middle vent hole, at a position corresponding to the middle vent hole.

As a further improvement of the present invention, the whole blood filter cavity is provided with a sample inlet part to be connected with external gas, the sample inlet part is provided with a sample introduction port and riser vents, and the distance from each said riser vent to a bottom of the whole blood filter cavity is greater than the distance from the sample introduction port to the bottom of the whole blood filter cavity.

As a further improvement of the present invention, the sample inlet part is provided with an annular groove and an annular flange, an outer side wall of the annular flange is an inner side wall of the annular groove, and an air source connector is disposed in the annular groove; and the riser vents include a first riser vent and a second riser vent, the first riser vent is formed in an end face of the annular flange connected with the a sample introduction port through a convergence transition face, the second riser vent is formed in the convergence transition face and is next to an inner wall of the annular flange, and the second riser vent is adjacent to the first riser vent in position.

As a further improvement of the present invention, the whole blood filter cavity includes a whole blood sample filter tank and a top cover for sealing the whole blood sample filter tank, and the sample inlet part is disposed on the top cover; the whole blood sample filter tank is provided with a filtered sample outlet and has a side wall extending to the filtered sample outlet in a gradually converging mode, and the side wall extending in the gradually converging mode is provided with teeth used for guiding flow; and whole blood sample filter paper is laid in the whole blood sample filter tank, and a side edge of the whole blood sample filter paper makes contact with internal tips of the adjacent teeth on the tooth-shaped side wall of the whole blood sample filter cavity.

The other technical object of the present invention is to provide a single-channel chemiluminescent micro-fluidic chip, including a chip body; characterized in that the chip body is of a three-piece structure and includes an upper chip layer, a middle chip layer and a lower chip layer sequentially stacked together from top to bottom, and every two of the upper chip layer, the middle chip layer and the lower chip layer are stacked together through cooperative connection of positioning columns and positioning holes; wherein:

a whole blood filter tank, a quantification-reaction pool and a waste liquid pool are disposed on the lower chip layer, a fluid outlet of the whole blood filter tank is sequentially communicated with the quantification-reaction pool and the waste liquid pool through a micro-fluidic passage, a fluid inlet of the quantification-reaction pool is communicated with corresponding external fluid paths through a cleaning solution delivery branch and a chromogenic reagent delivery branch respectively, and the whole blood filter tank is communicated with an external air path;

the quantification-reaction pool is equally divided into three cavities by two partition plates a disposed perpendicular to a fluid flow direction, a labeled antibody is placed in the middle cavity, and coated antibodies are placed in the partitioned cavities on two sides; and a surface, facing the quantification-reaction pool, of the reaction pool cover plate is equally divided into two cover plate parts by a partition plate b disposed perpendicular to the fluid flow direction, and the coated antibodies are embedded in the cover plate parts;

the middle chip layer is provided with a sample inlet part at a position corresponding to the whole blood filter tank, the reaction pool cover plate, used for sealing an opening of the quantification-reaction pool, is disposed at a position corresponding to the quantification-reaction pool, a middle cover plate, used for sealing an opening of the waste liquid pool, is disposed at a position corresponding to the waste liquid pool, a cleaning solution connector is disposed at a position corresponding to a fluid inlet of the cleaning solution delivery branch, and a chromogenic reagent connector is disposed at a position corresponding to a fluid inlet of the chromogenic reagent delivery branch;

the upper chip layer is provided with a sample inlet part through hole at a position corresponding to the sample inlet part, an optical path scanning window is disposed at a position corresponding to the reaction pool cover plate, an upper cover plate is disposed at a position corresponding to the middle cover plate, a cleaning solution connector through hole is disposed at a position corresponding to the cleaning solution connector, and a chromogenic reagent connector through hole is disposed at a position corresponding to the chromogenic reagent connector;

a first anti-backflow device is disposed at the micro-fluidic passage between the whole blood filter tank and the quantification-reaction pool, and a second anti-backflow device is disposed on the micro-fluidic passage from a junction of the cleaning solution delivery branch and a chromogenic reagent delivery branch to the quantification-reaction pool;

the first anti-backflow device and the second anti-backflow device are of a same structure and each includes an anti-backflow structure located above the micro-fluidic passage and provided with an anti-backflow passage for increasing a liquid level of the micro-fluidic passage at an anti-backflow structure mounting position; and when the micro-fluidic passage is communicated with the external air path, fluid in the micro-fluidic passage on both sides of each said anti-backflow device is driven by air from the external air path to circulate by overcoming a pressure generated by the liquid level, increased by the corresponding anti-backflow passage at the corresponding anti-backflow structure mounting position, of the micro-fluidic passage;

a valve device is disposed on the micro-fluidic passage between the quantification-reaction pool and the waste liquid pool and includes a detection mechanism used to sense whether or not fluid flows through a valve device mounting position; the valve device in a normally-open state in the chip body automatically closes to be in an interruption state when a numerical value fed back by the detection mechanism indicates that fluid flows through the valve device mounting position, and the valve device in the interruption state can be regularly opened to be in a circulation state; and when the valve device is in the circulation state, fluid is pushed by air flow from the external air path to circulate in the valve device.

Another technical object of the present invention is to provide a detection method, of a single-channel chemiluminescent micro-fluidic chip, characterized by including the following steps:

Step 1, add a whole blood sample into a whole blood filter cavity via a sample introduction port;

Step 2, after a chip body is incubated for a period of time t1, make the chip body in contact with an external air path, external fluid paths and a pressing mechanism, so that a cleaning solution delivery branch and a chromogenic reagent delivery branch of the chip body are communicated with the corresponding external fluid paths and the whole blood filter cavity is communicated with the external air path, and that in a valve device, a pressing head of a pressing mechanism makes contact with an inner sealing film of a conductive sealing ring and a capacitance probe makes contact with a capacitance probe contact of the conductive sealing ring;

Step 3, slowly inflate the chip body by the external air path, so that the whole blood sample is promoted to turn into plasma after being filtered by whole blood filter paper and then enters the whole blood filter cavity;

Step 4, under the continuous air pressure from the external air path, the plasma in the whole blood filter cavity continues to flow forward through a first anti-backflow device and a quantification-reaction cavity in sequence along a micro-fluidic passage and then to flow into the valve device, at this moment, trigger the valve device to close the micro-fluidic passage once the plasma touches the conductive sealing ring of the valve device and then the capacitance probe senses capacitance changes of the capacitance probe contact, in contact with the capacitance probe, of the conductive sealing ring, and at the same time, close the external air path to stop pressurization;

Step 5, separate the chip body from the external air path, the external fluid paths and the pressing mechanism, and evenly mix the plasma in the quantification-reaction cavity with coated antibodies and a labeled antibody is embedded in the quantification-reaction cavity for 3-10 minutes for an immune reaction;

Step 6, make the chip body in contact with the external air path, the external fluid paths and the pressing mechanism, so that the cleaning solution delivery branch and the chromogenic reagent delivery branch of the chip body are communicated with the corresponding external fluid paths and the whole blood filter cavity is communicated with the external air path, and that in the valve device, the pressing head of the pressing mechanism makes contact with the inner sealing film of the conductive sealing ring and the capacitance probe makes contact with the capacitance probe contact of the conductive sealing ring;

Step 7, start the external air path, so that the plasma in the chip body is pushed by an air pressure from the external air path to flow along the micro-fluidic passage till the plasma in the sample introduction port and the micro-fluidic passage is dried, and at this moment, close the external air path when a capacitance value sensed by the capacitance probe returns to an initial value;

Step 8, start a cleaning solution device in the corresponding external fluid path to make a cleaning solution sequentially flow through the second anti-backflow device disposed on the cleaning solution delivery branch and the quantification-reaction cavity to reach the valve device, trig the valve device to close the micro-fluidic passage once the cleaning solution touches the conductive sealing ring of the valve device and then the capacitance probe senses capacitance changes of the capacitance probe contact, in contact with the capacitance probe, of the conductive sealing ring, and at the same time, close the external air path to stop pressurization;

Step 9, evenly mix the cleaning solution in the chip body and particularly in the quantification-reaction cavity for 1-3 minutes for cleaning;

Step 10, start the external air path to provide an air pressure to push the cleaning solution to flow forwards to dry the chip body, and close the external air path when a capacitance value sensed by the capacitance probe returns to the initial value;

Step 11, repeat steps 8-10 for 3-8 times;

Step 12, start a chromogenic reagent device in the corresponding external fluid path to make a chromogenic reagent sequentially flow through the anti-backflow device disposed on the chromogenic reagent delivery branch and the quantification-reaction cavity to reach the valve device, trig the valve device to close the micro-fluidic passage once the chromogenic reagent touches the conductive sealing ring of the valve device and then the capacitance probe senses capacitance changes of the capacitance probe contact, in contact with the capacitance probe, of the conductive sealing ring, and at the same time, close the external air path to stop pressurization;

Step 13, evenly mix the chromogenic reagent in the quantification-reaction cavity for 3-8 minutes for a color development reaction; and Step 14, separate the chip body from the external air path, the external fluid paths and the pressing mechanism to complete detection.

Based on the above technical scheme, the present invention has the following advantages over the prior art:

A quantification-reaction cavity of a special structure is provided by the present invention and can contain coated antibodies and a labeled antibody at the same time, and meanwhile, the coated antibodies and the labeled antibody are physically separated (through a partition plate a and a partition plate b, and the coated antibodies placed in a reaction pool cover plate are spaced from the labeled antibody placed in a quantification-reaction pool), so that the reagent operation process is simplified, and nonspecific binding of the coated antibodies and the labeled antibody is effectively avoided. Furthermore, through the partition plate a and the partition plate b in the quantification-reaction cavity, fluid flow passing through the quantification-reaction cavity is made wavy to well mix the coated antibodies and the labeled antibody, and thus, testing efficiency and sensitivity are effectively improved.

1. Anti-backflow devices (a first anti-backflow device and a second anti-backflow device) are assembled at the front end of the fluid inlet of the quantification-reaction cavity so that the multiple micro-fluidic chips can be operated by one instrument to achieve a multi-flux result; by the fact that the anti-backflow devices prevent fluid from flowing backwards even if thrust for making the fluid flow forwards is removed, during the incubation time of different steps, one micro-fluidic chip can be taken from the instrument, and the other micro-fluidic chip can be operated by the instrument to achieve the multi-flux effect.

2. A valve device is assembled at the rear end of the quantification-reaction cavity and is closely combined with the instrument, the valve can be opened and closed at any time through a sealing ring with a sealing film and a pressing device on the instrument, and the valve device can be repeatedly used. Meanwhile, large-scale protrusion is ensured, and the requirement of the valve device for the protrusion process is not very high. Furthermore, the time when the fluid in the passage flows to the sealing ring can be detected in time to accurately close the sealing ring, so that bubbles in front of the fluid are removed, the fluid is throttled, and the effect of a semi-permeable film (permeable to air, but not to fluid) device is achieved. A function module of the semi-permeable film device is no longer needed.

3. A whole blood filter cavity is provided with a sample introduction port and riser vent in a sample inlet part, so that the blockage of a whole blood sample caused by active micro-fluidic is avoided; the riser vent include a second riser vent and a first riser vent at different altitudes, the distance from the second riser vent to the bottom of the whole blood filter cavity is greater than the distance from the sample introduction port to the bottom of the whole blood filter cavity, and particularly, the first riser vent is higher than the second riser vent, so that in the sample adding process, even if the sample introduction port and the second riser vent are both blocked, the whole blood filter cavity can still be communicated with an air source through the first riser vent to ensure the circulation of an active micro-fluidic air path.

4. The side wall of a whole blood sample filter tank extends to a filtered sample outlet in a gradually converging mode to achieve a flow guiding effect; and the side wall extending in the gradually converging mode is provided with teeth used for guiding flow, so that the problem that a whole blood sample cannot be completely filtered due to the presence of a gap (the gap between the side wall of the whole blood sample filter tank and the side edge of whole blood sample filter paper) caused by production errors is effectively avoided.

5. The waste liquid cavity is provided with an air flow channel, and the air is exhausted through an air outlet of the waste liquid cavity, so that it is effectively ensured that fluid is well absorbed by absorbent paper so as to be prevented from flowing backwards, splashing outwards or leaking.

BRIEF DESCRIPTION OF THE SEVERAL VIEWS OF THE DRAWINGS

In FIG. 1: 1, upper chip layer; 2, middle chip layer; 3, lower chip layer; 4, external air path; 5, external fluid path; 5-1, sealing gasket; 6-1, pressing mechanism; 6-2, conductive sealing ring; 7-1, second absorbent paper; 7-2, first absorbent paper; 8, blood filter paper;

In FIG. 2 and FIG. 3: 3-1, whole blood filter tank; 3-1-1, sample guiding component; 3-2, quantification-reaction pool; 3-2-1, partition plate a; 3-3, waste liquid pool; 3-3-1, waste liquid guiding components; 3-3-2, absorbent paper positioning columns; 3-4, cleaning solution delivery branch; 3-5, chromogenic reagent delivery branch; 3-6, lower chip layer outer positioning port; 3-7, chip fixing column; 6, valve device; 9-a, first anti-backflow device; 9-b, second anti-backflow device;

Figure 1:
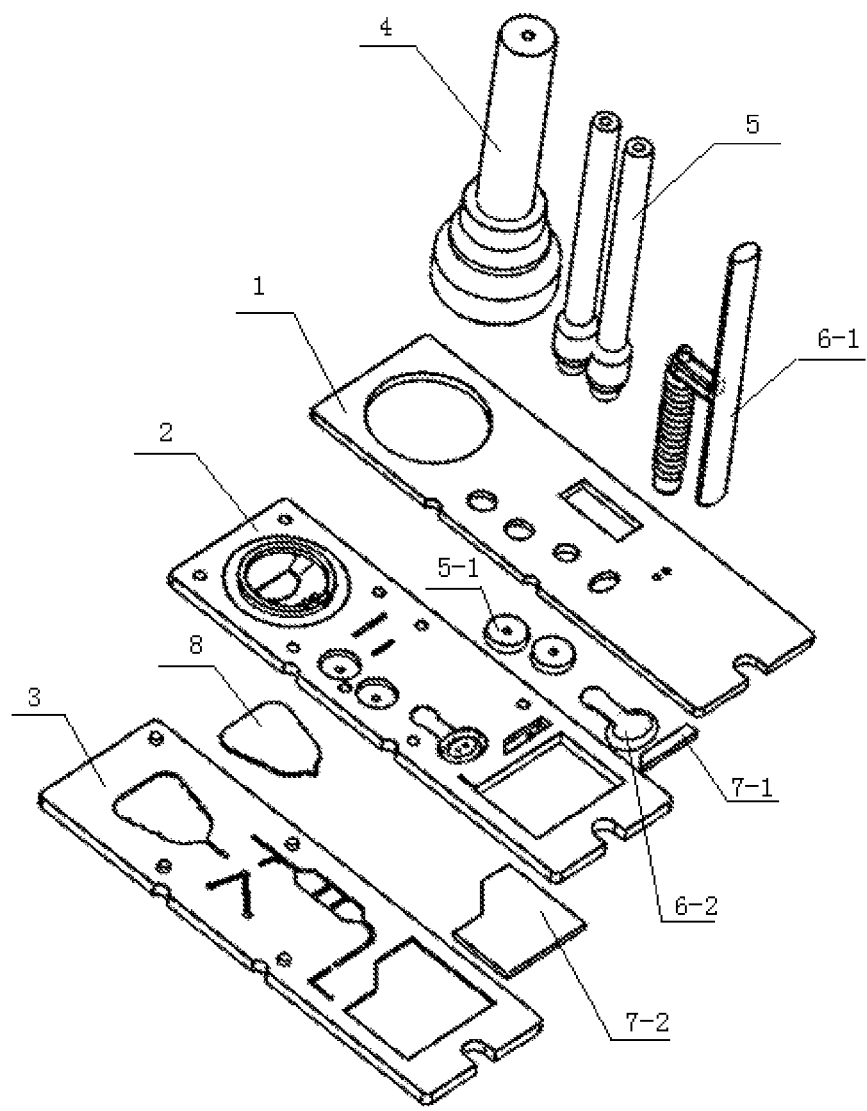
FIG. 1 is an exploded view of a single-channel chemiluminescent micro-fluidic chip of the present invention.
Figure 2:
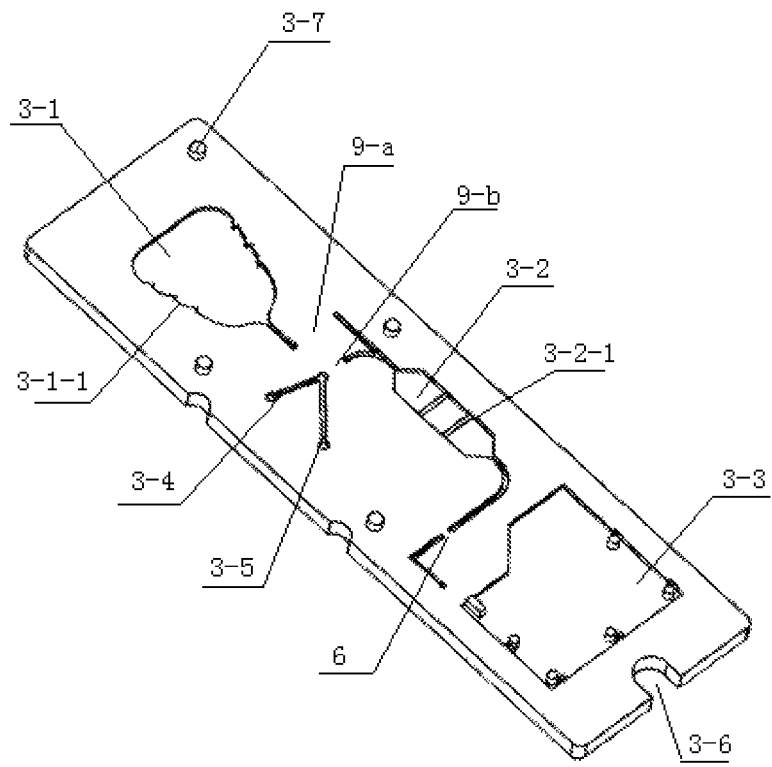
FIG. 2 is a structural view of a lower chip layer of the present invention.
Figure 3:
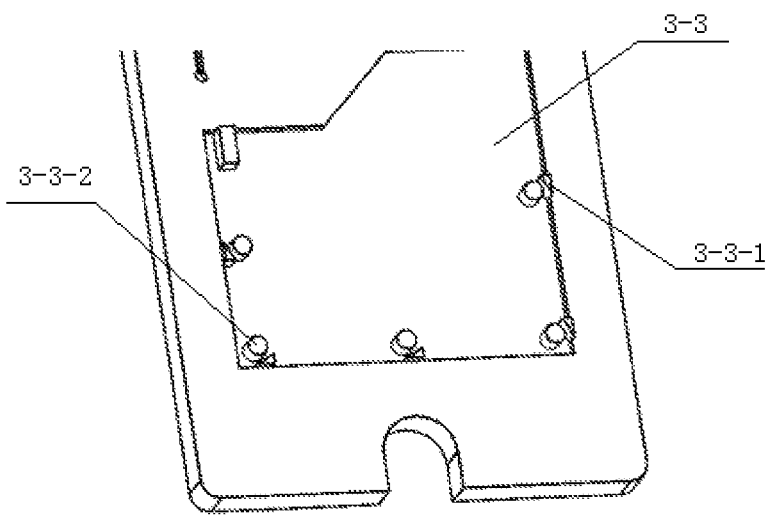
FIG. 3 is an enlarged view of a waste liquid pool (without absorbent paper) in FIG. 2.
Figure 4:
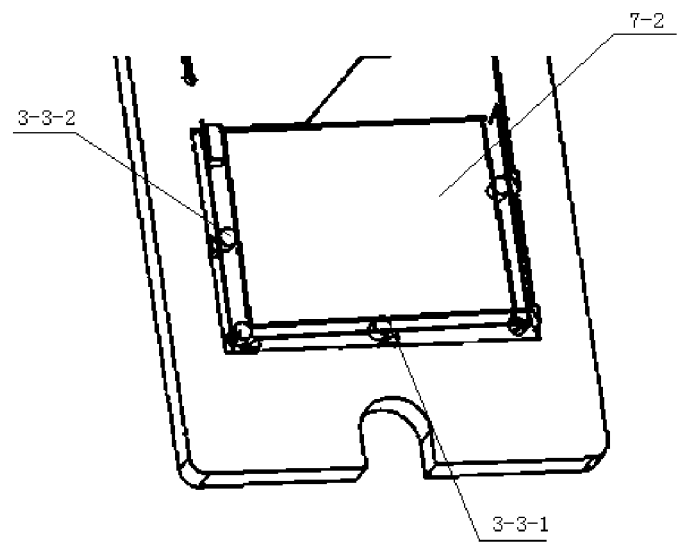
FIG. 4 is an enlarged view of the waste liquid pool (with absorbent paper) in FIG. 2.
Figure 5:
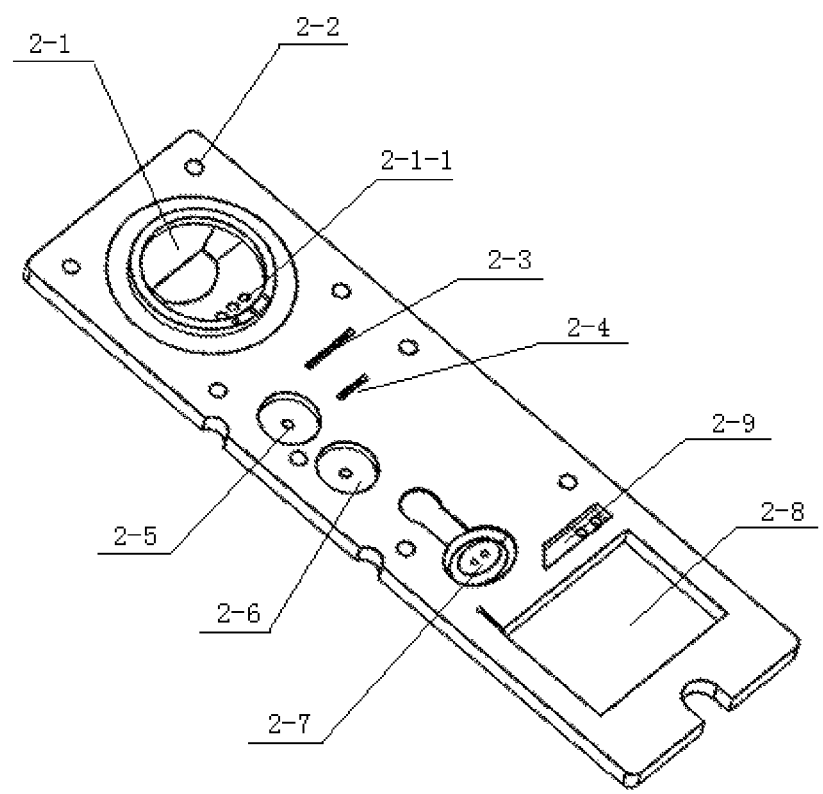
Figure 6:
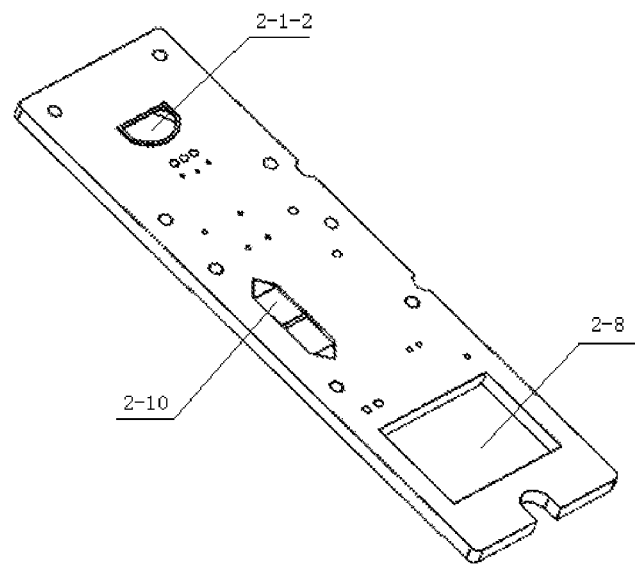
Figure 7:
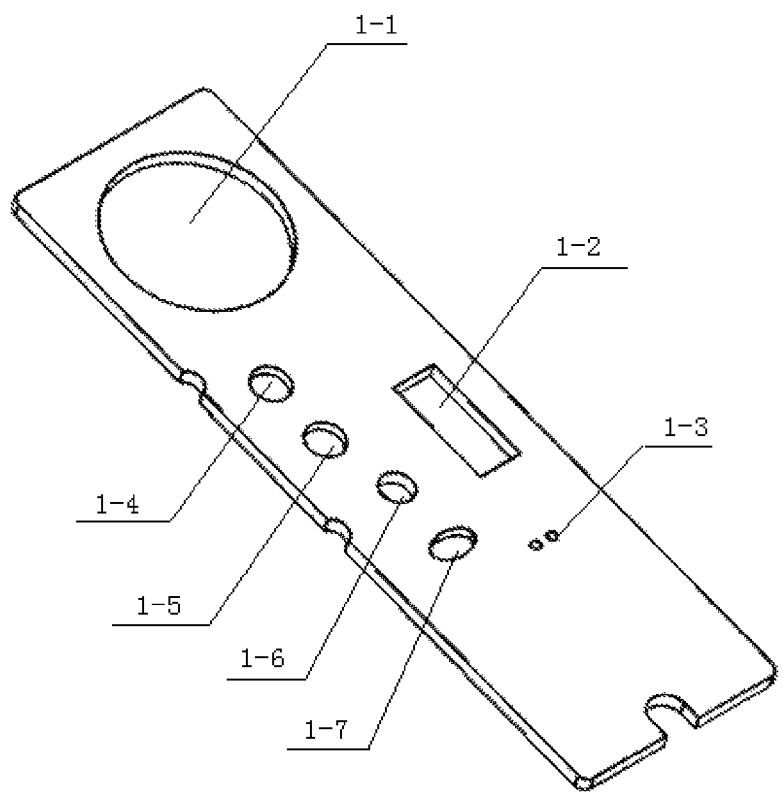
Figure 8:
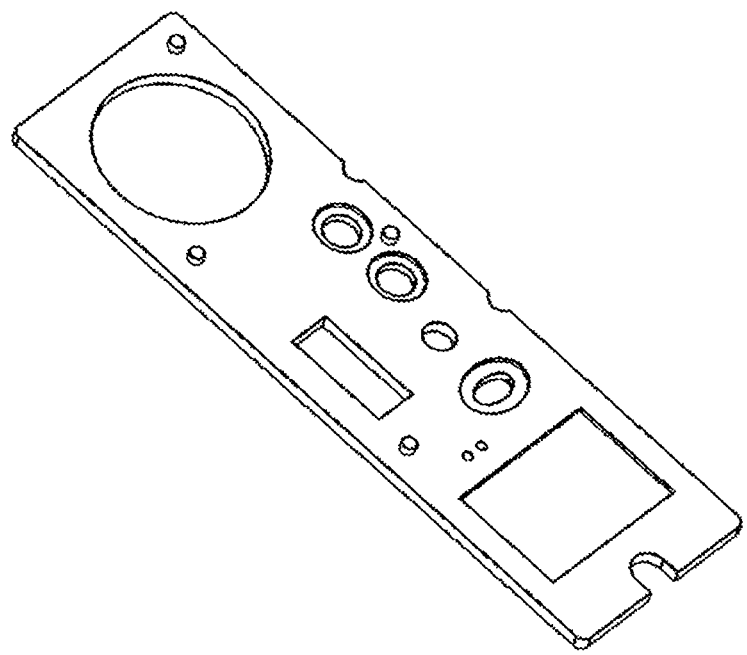
Figure 9:
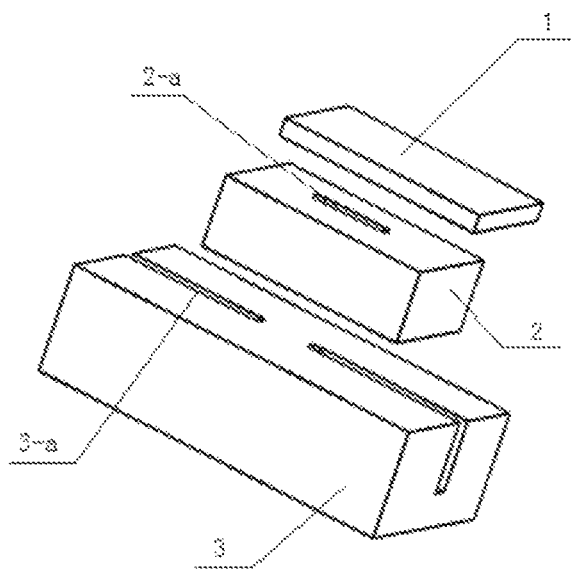
Figure 10:
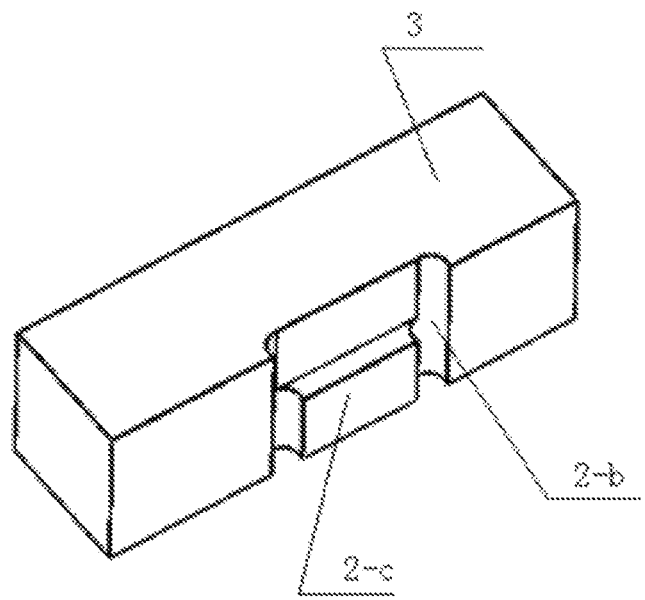
Figure 11:
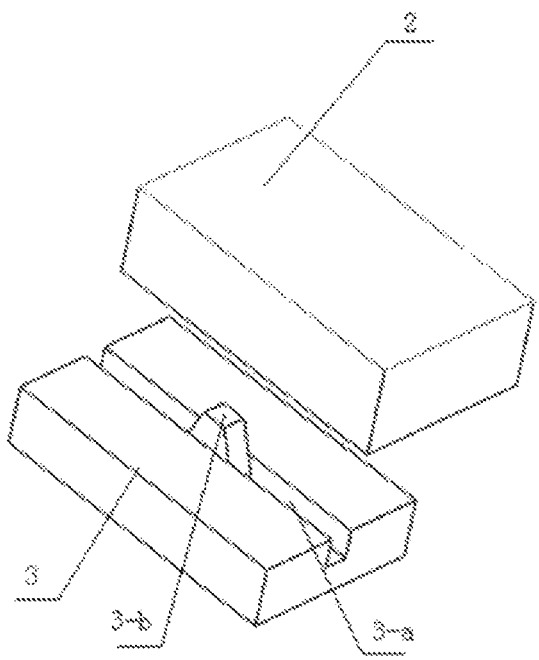
Figure 12:
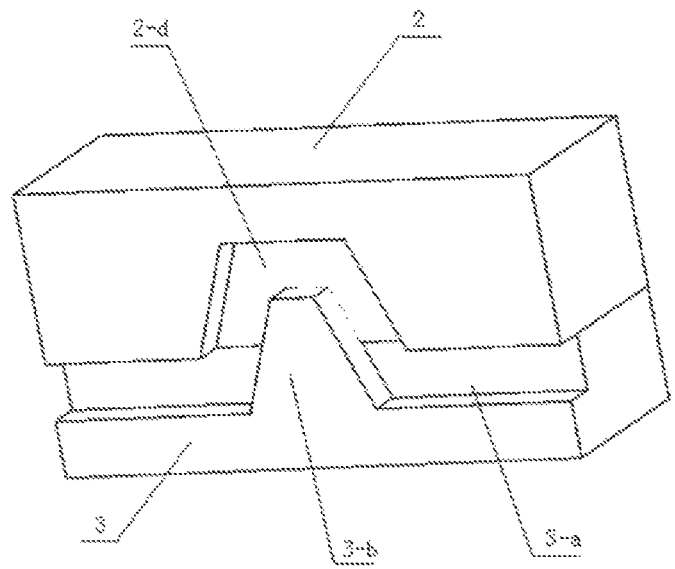
Figure 13:
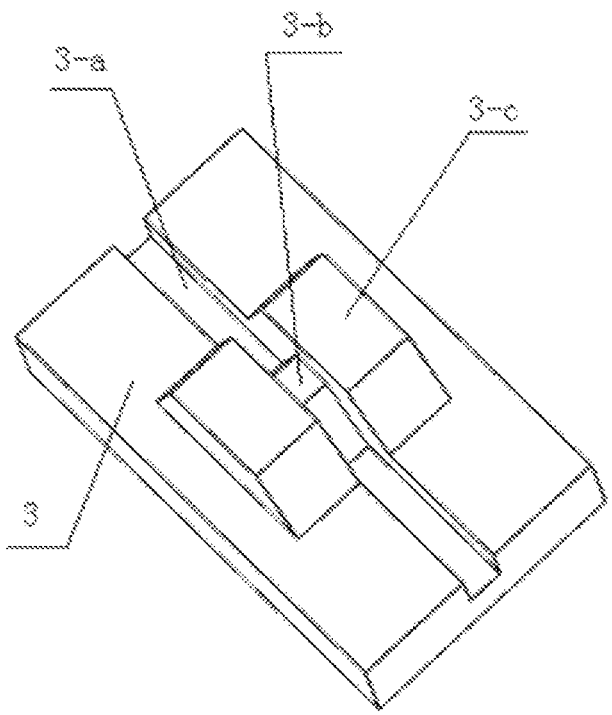
Figure 14:
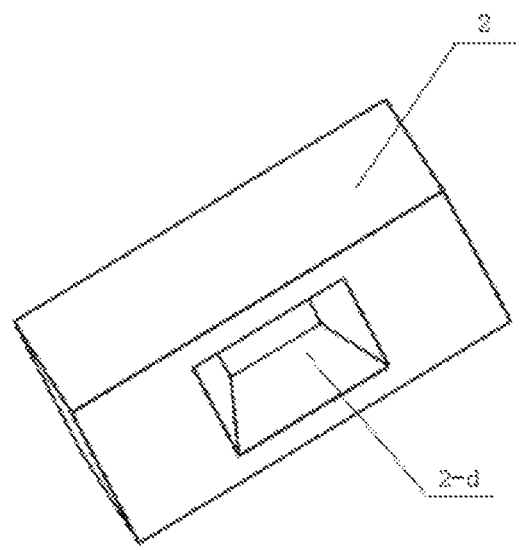
Figure 15:
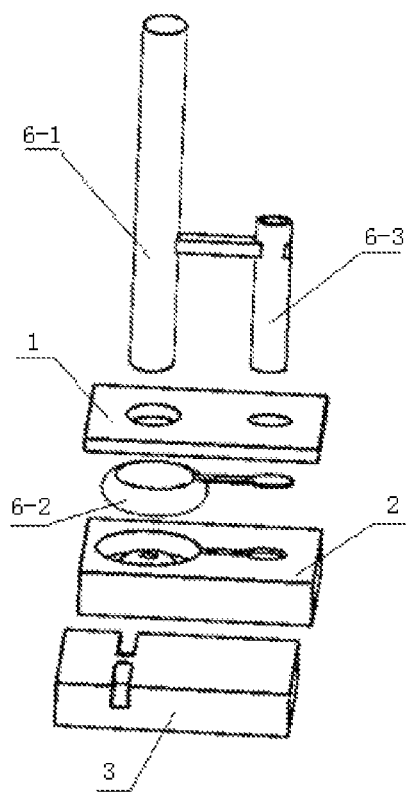
Figure 16:
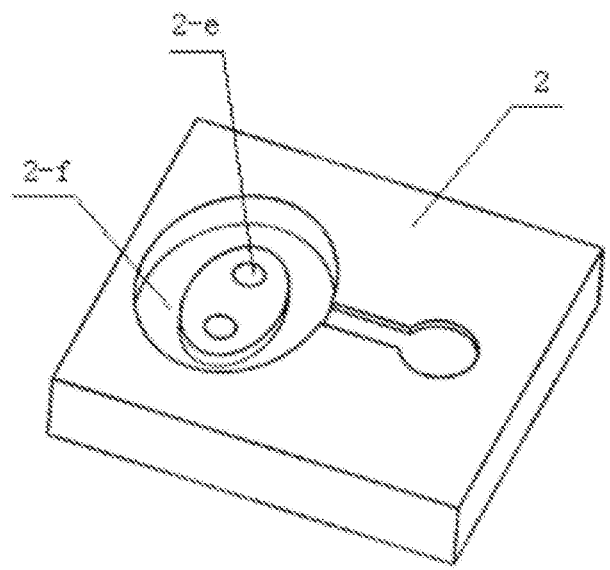
Figure 17:
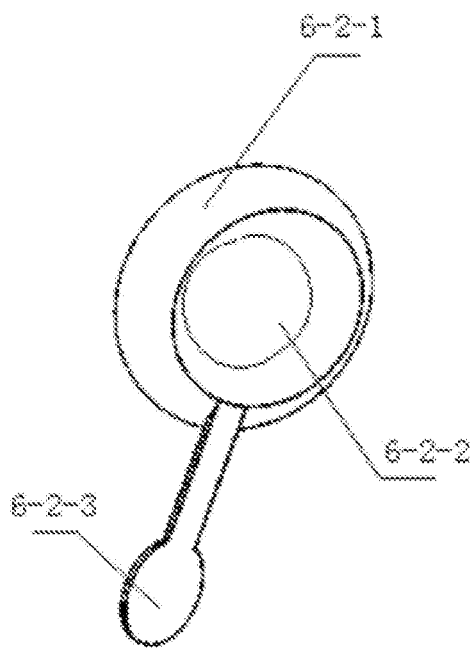
Figure 18:
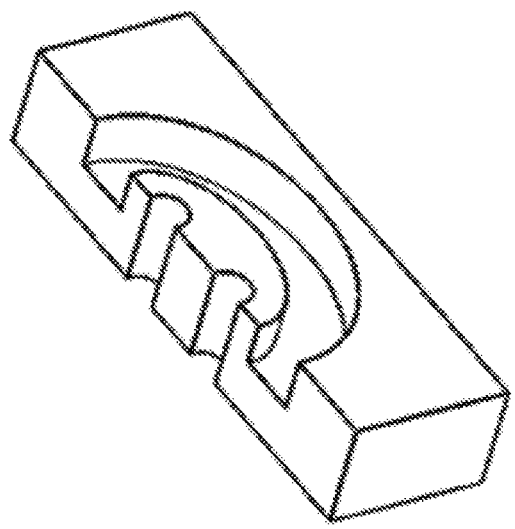
Figure 19:
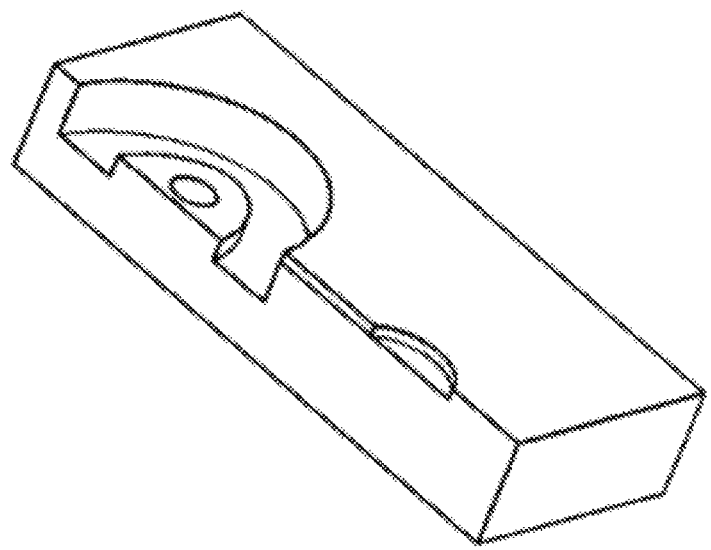

The arrow direction in FIG. 4 indicates an air flow channel in the waste liquid pool;

FIG. 5 is a structural view of a middle chip layer in one direction (front side);

FIG. 6 is a structural view of the middle chip layer in another direction (back side);

Particularly: 2-1, sample loading slot; 2-1-1, riser vent; 2-1-2, sample introduction port; 2-2, chip positioning hole; 2-3, backflow hole of first anti-backflow device; 2-4, backflow hole of second anti-backflow device; 2-5, external connector of cleaning solution branch; 2-6, external connector of chromogenic reagent branch; 2-7, mounting groove of conductive sealing ring; 2-8, middle through hole of waste liquid pool; 2-9, air outlet; 2-10, reaction pool cover plate;

FIG. 7 is a structural view of the front side of an upper chip layer;

FIG. 8 is a structural view of the back side of the upper chip layer;

In FIG. 7 and FIG. 8: 1-1, through hole of sample inlet part; 1-2, optical path scanning window; 1-3, riser vent of waste liquid pool; 1-4, through hole of cleaning solution external connector; 1-5, through hole of chromogenic reagent external connector; 1-6, capacitance probe penetration hole; 1-7, pressing head penetration hole;

FIG. 9 is a structural view of a three-piece anti-backflow structure;

FIG. 10 is a sectional view of FIG. 9;

FIG. 11 is a structural view of an anti-backflow structure of a second structural form;

FIG. 12 is a sectional view of FIG. 11;

FIG. 13 is a structural view of a lower chip layer in an anti-backflow structure of a third structural form;

FIG. 14 is a structural view of an upper chip layer in the anti-backflow structure of the third structural form;

In FIGS. 9-14: 1, upper chip layer; 2, middle chip layer; 2-a, anti-backflow fluid outlet; 2-b, anti-backflow communication passage; 2-c, anti-backflow protrusion; 2-d, anti-backflow passage; 3, lower chip layer; 3-a, micro-fluidic passage; 3-b, micro-fluidic passage partition block; 3-c, connection column;

FIG. 15 is an exploded view of a valve device of the present invention;

FIG. 16 is a structural view of a middle chip layer at a position corresponding to the valve device;

FIG. 17 is a perspective view of a conductive sealing ring;

FIG. 18 is a sectional view of FIG. 16 in one direction;

FIG. 19 is a sectional view of FIG. 16 in another direction;

In FIGS. 15-19: 1, upper chip layer; 2, middle chip layer; 2-e, middle chip layer passage; 2-f, sealing ring groove; 3, lower chip layer; 6-1, pressing mechanism; 6-2, conductive sealing ring; 6-2-1, outer sealing ring; 6-2-2, inner sealing film; 6-2-3, capacitance probe contact; 6-3, detection probe.

DETAILED DESCRIPTION OF THE INVENTION

A clear and complete description of the technical scheme of the embodiments of the present invention is given as follows in combination with the drawings in the embodiments. Obviously, the embodiments in the following description are only part of embodiments of the present invention instead of being all embodiments of the present invention. The following description of at least one embodiment by a typical example is actually illustrative solely and is by no means restrictive to the present invention and application or use of the present invention. All other embodiments obtained based on the embodiments of the present invention by those ordinarily skilled in this field without creative work should fall within the protection scope of the present invention. Without additional specifications, relative configurations of components and steps, expressions and numerical values mentioned in these embodiments do not limit the scope of the present invention. Meanwhile, it would appreciate that for a brief description, the components in these figures are drawn not to an actual scale. Techniques, methods and devices known by those ordinarily skilled in relevant fields will possibly not be discussed in detail anymore hereinafter; however, where appropriate, these techniques, methods and devices should be regarded as part of this authorized specification. In all these provided and discussed embodiments, any concrete values should be interpreted as illustrative solely instead of being interpreted as restrictive. Thus, different values are available in other illustrative embodiments.

For a brief description, spatial relative terms such as 'on', 'above', 'on an upper surface' and 'upper' may be used here to explain spatial position relations between one device or characteristic and the other device or characteristic shown in the figures. It would appreciate that these spatial relative terms are intended to include different positions except the position of the device in the figures in use or operation. For instance, if devices in the figures are reversed, the description should be 'on a lower portion of the other device or configuration' or 'below the other device or configuration' based on a previous description 'on an upper portion of the other device or configuration' or 'above the other device or configuration'. Thus, the illustrative term 'above' may include a position 'above' and a position 'below'. The devices can also be positioned in other different ways (rotated by 90° or located at other positions).

One specific embodiment of the present invention is shown in detail by the drawings. The technical scheme of the present invention is explained in detail in combination with the drawings as follows.

A whole blood sample filter tank is provided with a filtered sample outlet and has a side wall extending to the filtered sample outlet in a gradually converging mode. The side wall extending in the gradually converging mode is provided with teeth used for guiding flow. Whole blood sample filter paper is laid in the whole blood sample filter tank, and the side edge of the whole blood sample filter paper makes contact with inner convex tips of the adjacent teeth on the tooth-shaped side wall of the whole blood sample filter tank. The whole blood sample filter paper is tightly pressed against the bottom of the whole blood sample filter tank through sample filter paper pressing points disposed at the lower end of a sample inlet part.

A waste liquid pool, as shown in FIG. 4, is provided with a waste liquid pool part a and a waste liquid pool part b which are communicated with each other. A plurality of waste liquid guiding components are disposed on the wall of the waste liquid pool part a, and absorbent paper fixing columns are disposed at the bottom of the waste liquid pool part a and are next to the waste liquid guiding components. The waste liquid guiding components are each in an arc tooth shape and are sequentially disposed on the wall of the waste liquid pool part a in respective arc directions. First absorbent paper is disposed in the waste liquid pool through the absorbent paper fixing columns, and the side edge of the first absorbent paper makes contact with tips of the waste liquid guiding components.

A middle cover plate is provided with a middle through hole, communicated with the waste liquid pool part a, at a position corresponding to the waste liquid pool part a and a middle vent hole at a position corresponding to the waste liquid pool part b. An absorbent paper groove is formed in the position of the middle vent hole, and second absorbent paper is disposed in the absorbent paper groove.

The sample inlet part is provided with an annular groove and an annular flange. The outer side wall of the annular flange is the inner side wall of the annular groove. The annular flange is disposed on the upper surface of a middle chip layer. The outer side wall of the annular groove is located on an upper chip layer. The bottom of the annular groove is disposed on the middle chip layer and located between the outer side wall of the annular groove and the outer side wall of the annular flange. An air source connector is disposed in the annular groove. Riser vents include a first riser vent and a second riser vent, wherein the first riser vent is formed in the end face of the annular flange connected with a sample introduction port through a conical transition face, and the second riser vent is formed in the conical transition face and is next to the inner wall of the annular flange.

An upper cover plate is provided with a vent hole sealing cover, used for sealing the middle vent hole, at a position corresponding to the middle vent hole and is also provided with an upper vent hole, communicated with the middle vent hole, at a position corresponding to the middle vent hole.

The extension direction of an anti-backflow passage is perpendicular to the extension direction of a micro-fluidic passage at an anti-backflow structure mounting position. The micro-fluidic passage at the anti-backflow structure mounting position is partitioned by a micro-fluidic passage partition block into two sections, namely a micro-fluidic fluid inflow passage and a micro-fluidic fluid outflow passage. The anti-backflow passage has a closed upper end and a lower end stretching over the micro-fluidic passage partition block, and the upper end and the lower end of the anti-backflow passage are respectively communicated with the micro-fluidic fluid inflow passage and the micro-fluidic fluid outflow passage.

An anti-backflow protrusion is disposed in the anti-backflow passage, and two anti-backflow communication passages are formed between the anti-backflow protrusion and the anti-backflow passage and respectively communicated with the micro-fluidic fluid inflow passage and the micro-fluidic fluid outflow passage. The anti-backflow protrusion has a lower end flush with the lower end of the anti-backflow passages and an upper end lower than the upper end of the anti-backflow passages.

The anti-backflow protrusion between the two anti-backflow communication passages has a trapezoidal section.

The micro-fluidic passage partition block is a wedge block, and the anti-backflow passage is a wedge groove matched with the micro-fluidic passage partition block in shape.

The micro-fluidic passage at the anti-backflow structure mounting position is symmetrically provided with wedge-shaped connection columns on both sides of the micro-fluidic passage partition block. The anti-backflow passage is provided with wedge-shaped connection grooves cooperatively connected with the wedge-shaped connection columns.

A valve device is an anti-backflow micro-valve capable of preventing backflow and includes a pressing mechanism, a detection mechanism, a sealing component and a micro-valve anti-backflow structure, wherein:

The pressing mechanism includes a pressing head located above an inner sealing film.

The detection mechanism includes a detection probe which is in linkage connected with the pressing head and located above a probe contact, and the distance from the detection probe to the probe contact is smaller than the distance from the pressing head to the inner sealing film.

The sealing component is a conductive sealing ring and includes an outer sealing ring, an inner sealing ring and a capacitance probe contact, wherein the inner sealing film is located on an inner ring of the outer sealing ring, and the capacitance probe contact is connected with the outer sealing ring.

The micro-valve anti-backflow structure is separated from the micro-fluidic passage at the anti-backflow micro-valve mounting position and includes a micro-valve anti-backflow passage.

The micro-fluidic passage at the anti-backflow micro-valve mounting position is transversely partitioned by a micro-fluidic passage partition into a micro-valve fluid inflow section and a micro-valve fluid outflow section, wherein the micro-valve fluid inflow section is provided with a fluid outlet, and the micro-valve fluid outflow section is provided with a fluid inlet.

The micro-valve anti-backflow passage has a lower end disposed above the micro-fluidic passage partition and is correspondingly communicated with the fluid outlet of the micro-valve fluid inflow section and the fluid inlet of the micro-valve fluid outflow section.

According to the present invention, a micro-valve anti-backflow protrusion is disposed in an inner cavity of the micro-valve anti-backflow passage. A sealing ring groove for mounting the outer sealing ring is formed between an outer ring of the micro-valve anti-backflow protrusion and the inner cavity of the micro-valve anti-backflow passage. The micro-valve anti-backflow protrusion is provided with two communication passages, namely a micro-valve anti-backflow fluid inflow passage and a micro-valve anti-backflow fluid outflow passage. The lower end of the micro-valve anti-backflow fluid inflow passage is communicated with a fluid outlet of the micro-valve fluid inflow section. The lower end of the micro-valve anti-backflow fluid outflow passage is communicated with a fluid inlet of the micro-valve fluid outflow section. The outer sealing ring is embedded in the sealing ring groove. The inner sealing film covers the upper end of the micro-valve anti-backflow fluid inflow passage and the upper end of the micro-valve anti-backflow fluid outflow passage.

In the absence of anti-backflow structures, the inner sealing film can seal both the fluid outlet of the micro-valve fluid inflow section and the fluid inlet of the micro-valve outflow section and is sealed by the outer sealing ring.

Along with the pressing motion of the pressing mechanism, the detection probe of the detection mechanism makes contact with the capacitance probe contact to detect in real time whether or not fluid flows into the valve. At this moment, the anti-backflow micro-valve is in an open state. In fact, under the condition where the pressing head of the pressing mechanism is spaced from the inner sealing film, fluid is driven by air flow to enter the micro-valve outflow section from the micro-valve inflow section by overcoming deformation of the inner sealing film by the fact that the inner sealing film is deformable and a deformation space exists at the mounting position.

When the air path is opened, the fluid is driven by air pressure from the air path to flow forwards, the fluid in the micro-valve fluid inflow section passes through the micro-valve anti-backflow passage and then flows to the micro-valve fluid outflow section, the capacitance probe in the detection mechanism detects the fluid and triggers the pressing mechanism again, the inner sealing film is driven by the pressing mechanism to seal the upper end of the micro-valve anti-backflow passage, and at this moment, the anti-backflow micro-valve is in a closed state.

The detection mechanism includes a capacitance probe which can be driven by the pressing mechanism to be electrically connected with the capacitance probe contact.

Specifically, the pressing head of the pressing mechanism drives the detection probe to descend towards the conductive sealing ring, and the pressing mechanism stops descending when the detection probe makes contact with the probe contact, and at this moment, a gap exists between the pressing head and the inner sealing film; when data sensed by the detection probe changes, it indicates that fluid flows through the micro-fluidic passage at the valve device mounting position, the pressing mechanism is triggered to push the pressing head to continue to descend till the pressing head presses against the inner sealing film to cover the micro-valve fluid inflow section and the fluid inlet of the micro-valve fluid inflow section, and at this moment, the valve device is in an interruption state; and when a gap exists between the pressing head of the pressing mechanism and the inner sealing film, the valve device is in an open state, and the deformation characteristic of the inner sealing film ensures that fluid can flow out from the fluid outlet of the micro-valve fluid inflow section and can flow in from the fluid inlet of the micro-valve fluid outflow section.

As shown in the figures, the valve device is of a three-piece structure and includes an upper chip layer, a middle chip layer and a lower chip layer which are sequentially distributed from top to bottom. Every two of the upper chip layer, the middle chip layer and the lower chip layer are clamped together. The micro-valve anti-backflow structure is formed in the middle chip layer. The micro-fluidic passage is disposed on the lower chip layer. The groove corresponding to the micro-valve anti-backflow structure is formed in the upper surface of the middle chip layer. The sealing component is pressed in the groove through the upper chip layer. The upper chip layer is provided with a pressing head penetration hole at a position corresponding to the inner sealing ring and a probe penetration hole at a position corresponding to the detection contact. The pressing mechanism is located above the upper chip layer and can descend to drive the pressing head to pass through the pressing head penetration hole to press against the inner sealing film so as to seal the upper end of the micro-valve anti-backflow passage, and at this moment, the anti-backflow micro-valve is in a closed state; along with the pressing motion of the pressing mechanism 1, the capacitance probe moves towards the upper chip layer and then penetrates through the probe penetration hole in the upper chip layer to make contact with the probe contact of the conductive sealing ring in the groove of the middle chip layer so as to achieve electrical connection.

According to the present invention, the valve device is creatively designed and is combined with the anti-backflow devices used for micro-fluidic fluid control, so that the space of the micro-fluidic chip is saved. The positional space of the micro-fluidic chip is limited, and the space of the micro-fluidic passage of the present invention is effectively saved, so that the passage is designed more effectively. The problem that fluid in one fluid passage flows into another fluid passage due to a poor sealing effect of the passages which are too close to one another is solved.

According to the present invention, conductive rubber and the capacitance detection probe are combined to observe the accurate time when fluid in the passage flows to the valve, so that the valve is closed in time. A semi-permeable device is no longer needed.

Based on the above-mentioned single-channel chemiluminescent micro-fluidic chip, the present invention provides a following detection method. The detection method specifically includes the steps as follows:

Step 1, a reagent chip is inserted into an instrument, and information on the reagent chip is read;

Step 2, a sample is added through a pipettor, specifically, 100 ul of whole blood is added into the sample introduction port;

Step 3, the chip enters the instrument so as to be incubated for 2 minutes;

Step 4, the instrument is combined with contact devices, including an air path device, two fluid path devices and a valve pressing point with a conductive rubber probe, of the chip;

Step 5, the chip is slowly inflated by the air path device to push the whole blood sample to move forward, in the moving process, erythrocyte is intercepted by blood filter paper, the sample introduction port may be partially blocked by the erythrocyte under the air pressure and cannot allow air to pass through smoothly, and in this case, air enters the chip through the riser vents to push the sample to advance;

Step 6, after passing through the blood filter paper, the sample turns into plasma to enter the passage and then is pushed by the air pressure to pass through one anti-backflow device, and afterwards, the sample passes through the fluid passages; however, as the chip is tightly pressed by the fluid path devices at the tail ends of the fluid passage, fluid cannot enter the fluid passages, and the direction of the fluid passages is different from the flow direction of the sample;

Step 7, the sample continues to move forwards to enter a reaction-quantification hole;

Step 8, the sample keeps moving forward to enter the valve device, once the sample touches conductive rubber in the valve, a valve switch is triggered by capacitance change to close the passage valve, at this moment, the other anti-backflow device behind the valve is used to prevent fluid from being rapidly blown away, which may be caused if the valve is not closed in time, and at the same time, an air path switch is turned off to stop pressurization;

Step 9, the instrument is separated from the contact devices of the chip, and uniform mixing is conducted for 3-10 minutes for an immune reaction;

Step 10, the chip is combined with the contact devices of the chip again, so that the sample is pushed by air to move forward, the sample introduction port and the sample in the passage are dried, at this moment, data of the conductive rubber probe return to initial values, and the air path device is closed;

Step 11, the cleaning solution path device is started, so that a cleaning solution enters the passage and then is pushed by the pressure to pass through one anti-backflow device and afterwards to pass through the sample passage; however, as the chip is tightly pressed by the air path device at the tail end of the sample passage, fluid cannot enter this passage, and the direction of this fluid passage is different from the flow direction of the sample; meanwhile, as the chip is tightly pressed by the fluid path devices at the tail end of the other fluid passage, fluid cannot enter this passage either, and the direction of this fluid passage is also different from the flow direction of the sample;

Step 12, the cleaning solution continues to flow forwards to enter the reaction-quantification hole;

Step 13, the cleaning solution continues to flow forwards to enter the valve device, once the cleaning solution touches the conductive rubber in the valve, the valve switch is triggered by a capacitance change to close the passage valve, at this moment, the other anti-backflow device behind the valve is used to prevent the fluid from being rapidly blown away, which may be caused if the valve is not closed in time, and at the same time, the air path switch is turned off to stop pressurization;

Step 14, the cleaning solution is evenly mixed for 1-3 minutes for cleaning;

Step 15, air pushes the cleaning solution to flow forwards, the sample introduction port and the fluid passages are dried, and at this moment, data of the conductive rubber probe return to initial values, and the air path device is closed;

Step 16, steps 11-15 are repeated for 3-8 times;

Step 17, the chromogenic reagent path device is started, so that a chromogenic reagent enters the passage and then pushed by the pressure to pass through one anti-backflow device and afterwards to passes through the sample passage; however, as the chip is tightly pressed by the air path device at the tail end of the sample passage, fluid cannot enter the sample passage, and the direction of this fluid passage is different from the flow direction of the sample; meanwhile, as the chip is tightly pressed by the fluid path devices at the tail end of the other fluid passage, fluid cannot enter this fluid passage either, and the direction of this fluid passage is also different from the flow direction of the sample;

Step 18, the chromogenic reagent continues to flow forwards to enter the reaction-quantification hole;

Step 19, the cleaning solution continues to flow forwards to enter the valve device, once the cleaning solution touches the conductive rubber in the valve, the valve switch is triggered by a capacitance change to close the passage valve, at this moment, the other anti-backflow device behind the valve is used to prevent the fluid from being rapidly blown away, which may be caused if the valve fails to be closed timely, and at the same time, the air path switch is turned off to stop pressurization;

Step 20, the chromogenic reagent is evenly mixed for 3-8 minutes for a color development reaction;

Step 21, the instrument is separated from the contact devices of the chip;

Step 22, the instrument reads data;
Step 23, the chip retreats from the instrument to complete detection.

What is claimed is:

1. A single-channel chemiluminescent micro-fluidic chip, including a chip body, wherein the chip body includes an optical path scanning window, a whole blood filter cavity, a quantification-reaction cavity and a waste liquid cavity, a fluid outlet of the whole blood filter cavity is sequentially communicated with the quantification-reaction cavity and the waste liquid cavity through a micro-fluidic passage, the optical path scanning window is disposed over the quantification-reaction cavity, a fluid inlet of the quantification-reaction cavity is communicated with external fluid paths through a cleaning solution delivery branch and a chromogenic reagent delivery branch respectively, and the whole blood filter cavity is communicated with an external air path; characterized in that the quantification-reaction cavity is composed of a quantification-reaction pool on a lower portion and a reaction pool cover plate for sealing an opening of the quantification-reaction pool, the quantification-reaction pool is equally divided into three cavities by two partition plates a disposed perpendicular to a fluid flow direction, a labeled antibody is placed in the middle cavity, coated antibodies are placed in the partitioned cavities on two sides, a surface, facing the quantification-reaction pool, of the reaction pool cover plate is equally divided into two cover plate parts by a partition plate b disposed perpendicular to the fluid flow direction, and the coated antibodies are embedded in the cover plate parts.

2. The single-channel chemiluminescent micro-fluidic chip according to claim 1, wherein the fluid outlet of the whole blood filter cavity is communicated with the fluid inlet of the quantification-reaction cavity through a first anti-backflow device, and a fluid outlet of the cleaning solution delivery branch and a fluid outlet of the chromogenic reagent delivery branch are converged and then communicated with the fluid inlet of the quantification-reaction pool through a second anti-backflow device; the first anti-backflow device and the second anti-backflow device are of the same structure and each includes an anti-backflow structure located above the micro-fluidic passage and provided with an anti-backflow passage for increasing a liquid level of the micro-fluidic passage at an anti-backflow structure mounting position; and when the micro-fluidic passage is communicated with the external air path, fluid in the micro-fluidic passage through both sides of each said anti-backflow device is driven by air from the external air path to circulate by overcoming a pressure generated by the liquid level, increased by the corresponding anti-backflow passage at the corresponding anti-backflow structure mounting position, of the micro-fluidic passage.

3. The single-channel chemiluminescent micro-fluidic chip according to claim 1, wherein a valve device is disposed on the micro-fluidic passage between the quantification-reaction cavity and the waste liquid cavity and includes a detection mechanism used to sense whether or not fluid flows through a valve device mounting position; the valve device in a normally-open state in the chip body automatically closes to be in an interruption state when a numerical value fed back by the detection mechanism indicates that fluid flows through the valve device mounting position, and the valve device in the interruption state is regularly opened to be in a circulation state; and when the valve device is in the circulation state, fluid is pushed by air flow from the external air path to circulate in the valve device.

4. The single-channel chemiluminescent micro-fluidic chip according to claim 1, wherein first absorbent paper is disposed in the waste liquid cavity, and the waste liquid cavity is provided with two waste cavity parts communicated with each other, namely a waste liquid cavity part a and waste liquid cavity part b, wherein an air flow channel is formed between an inner wall of the waste liquid cavity part a and the first absorbent paper, and the waste liquid cavity part b is provided with an air outlet.

5. The single-channel chemiluminescent micro-fluidic chip according to claim 4, wherein the waste liquid cavity includes a waste liquid pool, a middle cover plate for sealing an opening of the waste liquid pool, and an upper cover plate for covering the middle cover plate; a plurality of waste liquid guiding components are disposed on a wall, corresponding to the waste liquid cavity part a, of the waste liquid pool, and absorbent paper fixing columns are disposed at a bottom of the waste liquid pool and are adjacent to the waste liquid guiding components; the waste liquid guiding components are each in an arc tooth shape and sequentially disposed on the corresponding wall of the waste liquid pool in respective arc directions, the first absorbent paper is disposed in the waste liquid pool through absorbent paper fixing columns, and a side edge of the first absorbent paper makes contact with tips of the waste liquid guiding components; the middle cover plate is provided with a middle through hole, communicated with the opening of the waste liquid pool, at a position corresponding to the waste liquid cavity part a and a middle vent hole, communicated with the opening of the waste liquid pool, at a position corresponding to the waste liquid cavity part b; an absorbent paper groove is formed in a position of the middle vent hole, and second absorbent paper is disposed in the absorbent paper groove; and the upper cover plate is provided with a vent hole sealing cover, used to cover the middle vent hole, at a position corresponding to the middle vent hole and an upper vent hole, communicated with the middle vent hole, at a position corresponding to the middle vent hole.

6. The single-channel chemiluminescent micro-fluidic chip according to claim 1, wherein the whole blood filter cavity is provided with a sample inlet part to be connected with external gas, the sample inlet part is provided with a sample introduction port and riser vents, and the distance from each said riser vent to a bottom of the whole blood filter cavity is greater than the distance from the sample introduction port to the bottom of the whole blood filter cavity.

7. The single-channel chemiluminescent micro-fluidic chip according to claim 6, wherein the sample inlet part is provided with an annular groove and an annular flange, an outer side wall of the annular flange is an inner side wall of the annular groove, and an air source connector is disposed in the annular groove; and the riser vents include a first riser vent and a second riser vent, the first riser vent is formed in an end face of the annular flange connected with the a sample introduction port through a convergence transition face, the second riser vent is formed in the convergence transition face and is next to an inner wall of the annular flange, and the second riser vent is adjacent to the first riser vent in position.

8. The single-channel chemiluminescent micro-fluidic chip according to claim 6, wherein the whole blood filter cavity includes a whole blood sample filter tank and a top cover for sealing the whole blood sample filter tank, and the sample inlet part is disposed on the top cover; the whole blood sample filter tank is provided with a filtered sample outlet and has a side wall extending to the filtered sample outlet in a gradually converging mode, and the side wall extending in the gradually converging mode is provided with teeth used for guiding flow; and whole blood sample filter paper is laid in the whole blood sample filter tank, and a side edge of the whole blood sample filter paper makes contact with internal tips of the adjacent teeth on the tooth-shaped side wall of the whole blood sample filter cavity.

* * * * *